(12) United States Patent
Eyal et al.

(10) Patent No.: US 10,330,594 B2
(45) Date of Patent: Jun. 25, 2019

(54) NON-LINEAR FREQUENCY SCAN OPTICAL FREQUENCY-DOMAIN REFLECTOMETRY HAVING A PROCESSOR TO ESTIMATE A BACKSCATTERING PROFILE OF AN OPTICAL FIBER BY APPLYING A PREDEFINED FUNCTION TO A BEAT SIGNAL

(71) Applicants: DSIT SOLUTIONS LTD., Givat Shmuel (IL); RAMOT AT TEL-AVIV UNIVERSITY LTD., Tel Aviv (IL)

(72) Inventors: Avishay Eyal, Givat Shmuel (IL); Eyal Leviatan, Tel Aviv (IL); Meir Hahami, Petach Tikva (IL); Yakov Botsev, Rishon Lezion (IL)

(73) Assignees: DSIT SOLUTIONS LTD., Givat Shmuel (IL); RAMOT AT TEL-AVIV UNIVERSITY, Tel Aviv (IL)

( * ) Notice: Subject to any disclaimer, the term of this patent is extended or adjusted under 35 U.S.C. 154(b) by 92 days.

(21) Appl. No.: 15/549,180

(22) PCT Filed: Mar. 13, 2016

(86) PCT No.: PCT/IB2016/051426
§ 371 (c)(1),
(2) Date: Aug. 7, 2017

(87) PCT Pub. No.: WO2016/147100
PCT Pub. Date: Sep. 22, 2016

(65) Prior Publication Data
US 2018/0031471 A1    Feb. 1, 2018

Related U.S. Application Data

(60) Provisional application No. 62/133,392, filed on Mar. 15, 2015.

(30) Foreign Application Priority Data

Jan. 23, 2016 (IL) .......................................... 243731

(51) Int. Cl.
G01N 21/47 (2006.01)
G01M 11/00 (2006.01)
G01D 5/353 (2006.01)

(52) U.S. Cl.
CPC ....... G01N 21/474 (2013.01); G01M 11/3127 (2013.01); G01M 11/3172 (2013.01);
(Continued)

(58) Field of Classification Search
CPC .............. G01M 11/3172; G01M 11/39; G01D 5/3537; G01D 5/35358; H04B 10/071;
(Continued)

(56) References Cited

U.S. PATENT DOCUMENTS 4,840,481 A  *  6/1989  Spillman, Jr. ........... G01L 1/242
                                               250/227.17
5,062,703 A     11/1991  Wong et al.
(Continued)

FOREIGN PATENT DOCUMENTS

EP       2720388 A1   4/2014
WO    2013003141 A2   1/2013
WO    2016/075672 A1  5/2016

OTHER PUBLICATIONS

International Application # PCT/IB2016/051426 Search Report dated Jul. 10, 2016.
(Continued)

Primary Examiner — Que Tan Le
(74) Attorney, Agent, or Firm — Roach Brown McCarthy & Gruber, P.C.; Kevin D. McCarthy

(57) ABSTRACT

A system (20) for fiber-optic reflectometry includes an optical source (28, 40), a beat detection module (44, 48, 52,
(Continued)

56A, 56B) and a processor (36). The optical source is configured to generate a non-linearly-scanning optical interrogation signal having an instantaneous optical frequency that is a non-linear function of time. The beat detection module is configured to transmit the optical interrogation signal into an optical fiber (24), to receive from the optical fiber an optical backscattering signal in response to the optical interrogation signal, and to mix the optical backscattering signal with a reference replica of the optical interrogation signal, so as to produce a beat signal. The processor is configured (i) to hold a predefined function that is indicative of an expected phase of the beat signal resulting from the non-linearly-scanning optical interrogation signal as a function of position along the optical fiber and time, (ii) to estimate a backscattering profile of the optical fiber by applying the predefined function to the beat signal, and (iii) to sense one or more events affecting the optical fiber by analyzing the backscattering profile.

20 Claims, 4 Drawing Sheets

(52) U.S. Cl.
CPC ... *G01D 5/3537* (2013.01); *G01N 2021/4709* (2013.01); *G01N 2021/4742* (2013.01)

(58) Field of Classification Search
CPC ............ G01L 1/242; G01N 2021/4709; G01N 21/474
USPC .................................................... 250/227.14
See application file for complete search history.

(56) References Cited

U.S. PATENT DOCUMENTS

| 2007/0025432 | A1 | 2/2007 | Ozcan et al. |
| 2013/0094011 | A1 | 4/2013 | Barry et al. |
| 2014/0140691 | A1 | 5/2014 | Reaves et al. |

OTHER PUBLICATIONS

Zhou et al., "Distributed vibration sensing with time-resolved optical frequency-domain reflectometry", Optical Express, vol. 20, issue 12, pp. 13138-13145, year 2012.
Arbel et al., "Dynamic optical frequency domain reflectometry", Optics Express, vol. 22, issue 8, pp. 8823-8830, Apr. 7, 2014.
Bar-Am et al.,"OFDR with double interrogation for dynamic and quasi-distributed sensing", Optics Express, vol. 22, issue 3, pp. 2299-2308, Jan. 28, 2014.
Eickhoff et al., "Optical frequency domain reflectometry in single mode fiber", Applied Physics Letters, vol. 39, issue 9, pp. 693-695, Nov. 1, 1981.
Soller et al.,"Optical frequency domain reflectometry for single- and multi-mode avionics fiber-optics applications", IEEE Conference on Avionics, Fiber Optics and Photonics, pp. 38-39, year 2006.
Barfuss et al.,"Modified optical frequency domain reflectometry with high spatial resolution for components of integrated optic systems", Journal of Lightwave Technology, vol. 7, issue 1, pp. 3-10, year 1989.
Soller et al., "High resolution optical frequency domain reflectometry for characterization of components and assemblies", Optics Express, vol. 13, issue 2, pp. 666-674, Jan. 24, 2005.
Mussi et al., "152.5dB sensitivity high dynamic-range optical frequency domain reflectometry", Electronics Letters, issue 32, vol. 10, pp. 926-927, May 9, 1996.

Tsuji et al., "Coherent optical frequency domain reflectometry for a long single-mode optical fiber using a coherent lightwave source and an external phase modulator", IEEE Photonics Technology Letters, vol. 7, issue 7, pp. 804-806, Jul. 1995.
Fan et al., "Centimeter-level spatial resolution over 40 km realized by bandwidth-division phase-noise-compensated OFDR", Optics Express, vol. 19, pp. 19122-19128, Sep. 26, 2011.
Fan et al., "Phase-noise-compensated optical frequency domain reflectometry with measurement range beyond laser coherence length realized using concatenative reference method", Optics Letters, vol. 32, issue 22, pp. 3227-3229, Nov. 15, 2007.
Ito et al., "Long-range coherent OFDR with light source phase noise compensation", Journal of Lightwave Technology, vol. 30, issue 8, pp. 1015-1024, Apr. 15, 2012.
Passy et al., "Experimental and theoretical investigations of coherent OFDR with semiconductor laser sources", Journal of Lightwave Technology, vol. 12, issue 9, pp. 1622-1630, Sep. 1994.
Geng et al., "Narrow linewidth fiber laser for 100-km optical frequency domain reflectometry", IEEE Photonics Technology Letters, vol. 17, issue 9, pp. 1827-1829, Sep. 2005.
Li et al, "A linearly frequency modulated narrow linewidth single-frequency fiber laser", Laser Physics Letters, vol. 10, issue 7, 4 pages, May 23, 2013.
Leviatan et al., "High resolution DAS via sinusoidal frequency scan OFDR (SFS-OFDR)", ), Optics Express, vol. 23, issue 26, pp. 33318-33334, Dec. 17, 2015.
NKT Photonics, "Koheras Adjustik—Low noise, single frequency fiber laser benchtop systems", 3 pages, Oct. 19, 2016.
Corning, "Coming SMF-28 Ultra Optical Fiber", Product Information, 2 pages, Nov. 2014.
Thorlabs, "TW1550R5A2—Wideband Fiber Optic Coupler 1550 nm, 50:50 Ratio", 2 pages, May 25, 2017.
Kylia, "CPH24-X-90° optical hybrids", data sheet, 10 pages, Mar. 27, 2013.
Thorlabs, "6015-3-APC—Fiber Optic Circulators", Product Specification Sheet , 1 page, 1992-S01 Rev B, Mar. 27, 2009.
Zhou et al., "Optical fiber distributed vibration sensing system using time-varying gain amplification method", Optical Engineering, vol. 53, issue 8, Aug. 18, 2014.
Tateda et al., "Advances in optical time domain reflectometry", Journal of Lightwave Technology, vol. 7, issue 8, pp. 1217-1224, Aug. 1989.
Qin et al., "Distributed vibration/acoustic sensing with high frequency response and spatial resolution based on time-division multiplexing", Optics Communications, vol. 331, pp. 287-290, Nov. 15, 2014.
Mateeva et al., "Distributed acoustic sensing for reservoir monitoring with vertical seismic profiling", Geographical Prospecting, vol. 62, issue 4, pp. 679-692, Jul. 2014.
Hartog et al., "Vertical seismic optical profiling on wireline logging cable", Geographical Prospecting, vol. 62, issue 4, pp. 693-701 Jul. 2014.
He et al., "All Fiber Distributed Vibration Sensing Using Modulated Time-Difference Pulses", IEEE Photonics Technology Letters, vol. 25, issue 20, pp. 1955-1957, Oct. 15, 2013.
Tanimola et al., "Distributed fibre optic sensors for pipeline protection", Journal of Natural Gas Science and Engineering, vol. 1, issues 4-5, pp. 134-143, Nov. 2009.
Lu et al., "Distributed Vibration Sensor Based on Coherent Detection of Phase-OTDR", Journal of Lightwave Technology, vol. 28, issue 22, pp. 3243-3249, year 2010.
European Application # 16764310.5 search report dated Oct. 9, 2018.
Barnovski et al., "Fiber waveguides: a novel technique for investigating attenuation characteristics", Applied Optics, vol. 15, No. 9, pp. 2112-2115, Sep. 1, 1976.
Molenaar et al., "First Downhole Application of Distributed Acoustic Sensing for Hydraulic-Fracturing Monitoring and Diagnostics", SPE Drilling & Completion, vol. 27, issue 1, pp. 32-38, Mar. 2012.
Thorlabs., "Balanced Amplified Photo-detectors", PDB47xC, Operation Manual, version 1.3, 25 pages, Sep. 28, 2017.

* cited by examiner

NON-LINEAR FREQUENCY SCAN OPTICAL FREQUENCY-DOMAIN REFLECTOMETRY HAVING A PROCESSOR TO ESTIMATE A BACKSCATTERING PROFILE OF AN OPTICAL FIBER BY APPLYING A PREDEFINED FUNCTION TO A BEAT SIGNAL

FIELD OF THE INVENTION

The present invention relates generally to fiber-optic reflectometry, and particularly to methods and systems for fiber-optic reflectometry using non-linear frequency scanning.

BACKGROUND OF THE INVENTION

Fiber-optic reflectometry techniques are used for detecting and analyzing impairments and events that affect the optical properties of an optical fiber. Various fiber-optic reflectometry techniques are known in the art.

Some fiber-optic reflectometry techniques are based on Optical Frequency-Domain Reflectometry (OFDR). OFDR-based schemes are described, for example, by Zhou et al., in "Distributed vibration sensing with time-resolved optical frequency-domain reflectometry," Optical Express, volume 20, issue 12, 2012, pages 13138-13145; by Arbel and Eyal, in "Dynamic optical frequency domain reflectometry," Optics Express, volume 22, issue 8, 2014, pages 8823-8830; and by Bar-Am et al., in "OFDR with double interrogation for dynamic and quasi-distributed sensing," Optics Express, volume 22, issue 3, 2014, pages 2299-2308, which are incorporated herein by reference.

Additional OFDR schemes are suggested by Eickhoff and Ulrich, in "Optical frequency domain reflectometry in single mode fiber," Applied Physics Letters, volume 39, issue 9, 1981, pages 693-695; by Soller et al., in "Optical frequency domain reflectometry for single- and multi-mode avionics fiber-optics applications," IEEE Conference on Avionics, Fiber Optics and Photonics, 2006, pages 38-39; and by Barfuss and Brinkmeyer, in "Modified optical frequency domain reflectometry with high spatial resolution for components of integrated optic systems," Journal of Lightwave Technology, volume 7, issue 1, 1989, pages 3-10, which are incorporated herein by reference.

Yet additional OFDR techniques are described by Soller et al., in "High resolution optical frequency domain reflectometry for characterization of components and assemblies," Optics Express, volume 13, issue 2, 2005, pages 666-674; and by Mussi et al., in "−152.5 dB sensitivity high dynamic-range optical frequency domain reflectometry," Electronics Letters, issue 32, volume 10, 1996, pages 926-927, which are incorporated herein by reference.

Various techniques have been suggested for generating frequency-scanning optical signals used in OFDR. One approach uses an electro-optical modulator that is external to the laser. Such techniques are described, for example, by Tsuji et al., in "Coherent optical frequency domain reflectometry for a long single-mode optical fiber using a coherent lightwave source and an external phase modulator," IEEE Photonics Technology Letters, volume 7, issue 7, 1995, pages 804-806; by Fan et al., in "Centimeter-level spatial resolution over 40 km realized by bandwidth-division phase-noise-compensated OFDR," Optics Express, volume 19, 2011, pages 19122-19128; by Fan et al., in "Phase-noise-compensated optical frequency domain reflectometry with measurement range beyond laser coherence length realized using concatenative reference method," Optics Letters, volume 32, issue 22, 2007, pages 3227-3229; and by Ito et al., in "Long-range coherent OFDR with light source phase noise compensation," Journal of Lightwave Technology, volume 30, issue 8, 2012, pages 1015-1024, which are incorporated herein by reference.

A different approach for generating frequency-scanning optical signals is to directly modulate one of the laser parameters. Techniques of this sort are suggested, for example, by Passy et al., in "Experimental and theoretical investigations of coherent OFDR with semiconductor laser sources," Journal of Lightwave Technology, volume 12, issue 9, 1994, pages 1622-1630; by Geng et al., in "Narrow linewidth fiber laser for 100-km optical frequency domain reflectometry," IEEE Photonics Technology Letters, volume 17, issue 9, 2005, pages 1827-1829; and by Li et al, in "A linearly frequency modulated narrow linewidth single-frequency fiber laser," Laser Physics Letters, volume 10, issue 7, 2013, which are incorporated herein by reference.

SUMMARY OF THE INVENTION

An embodiment that is described herein provides a system for fiber-optic reflectometry. The system includes an optical source, a beat detection module and a processor. The optical source is configured to generate a non-linearly-scanning optical interrogation signal having an instantaneous optical frequency that is a non-linear function of time. The beat detection module is configured to transmit the optical interrogation signal into an optical fiber, to receive from the optical fiber an optical backscattering signal in response to the optical interrogation signal, and to mix the optical backscattering signal with a reference replica of the optical interrogation signal, so as to produce a beat signal. The processor is configured (i) to hold a predefined function that is indicative of an expected phase of the beat signal resulting from the non-linearly-scanning optical interrogation signal as a function of position along the optical fiber and time, (ii) to estimate a backscattering profile of the optical fiber by applying the predefined function to the beat signal, and (iii) to sense one or more events affecting the optical fiber by analyzing the backscattering profile.

In some embodiments, the instantaneous optical frequency of the optical interrogation signal is a sinusoidal function of time. In an embodiment, the predefined function specifies a complex conjugate of an exponential phase factor of the beat signal, which is expected to result from the non-linearly-scanning optical interrogation signal, as a function of the position and the time. In a disclosed embodiment, the processor is configured to hold a matrix of discrete values of the predefined function, and to apply the predefined function to the beat signal by multiplying the matrix by a vector of samples of the beat signal.

In some embodiments, the processor is configured to calculate multiple successive estimates of the backscattering profile, by applying the predefined function to multiple respective time periods of the beat signal, and to sense the events by analyzing the multiple successive estimates of the backscattering profile. In an example embodiment, the optical source is configured to generate the non-linearly-scanning optical interrogation signal with a given bandwidth and a given modulation frequency, and wherein the predefined function depends on the given bandwidth and the given modulation frequency. In an embodiment, the beat detection module is configured to mix the optical backscattering signal with the reference replica of the optical interrogation signal using In-phase/Quadrature (I/Q) mixing, such that the beat signal is complex-valued.

In some embodiments, the optical fiber is part of an optical communication system, and the one or more events include a fault in the optical fiber. In other embodiments, the optical fiber is part of a perimeter security system, and the one or more events include a breach of the perimeter security system. In yet other embodiments, the optical fiber is installed in a utility infrastructure, and the one or more events include a fault in the utility infrastructure.

There is additionally provided, in accordance with an embodiment of the present invention, a method for fiber-optic reflectometry. The method includes generating a non-linearly-scanning optical interrogation signal having an instantaneous optical frequency that is a non-linear function of time. The optical interrogation signal is transmitted into an optical fiber, and an optical backscattering signal is received from the optical fiber in response to the optical interrogation signal. The optical backscattering signal is mixed with a reference replica of the optical interrogation signal, so as to produce a beat signal. A backscattering profile of the optical fiber is estimated, by applying to the beat signal a predefined function that is indicative of an expected phase of the beat signal resulting from the non-linearly-scanning optical interrogation signal as a function of position along the optical fiber and time. One or more events affecting the optical fiber are sensed by analyzing the backscattering profile.

The present invention will be more fully understood from the following detailed description of the embodiments thereof, taken together with the drawings in which:

DETAILED DESCRIPTION OF EMBODIMENTS

Overview

Figure 1:
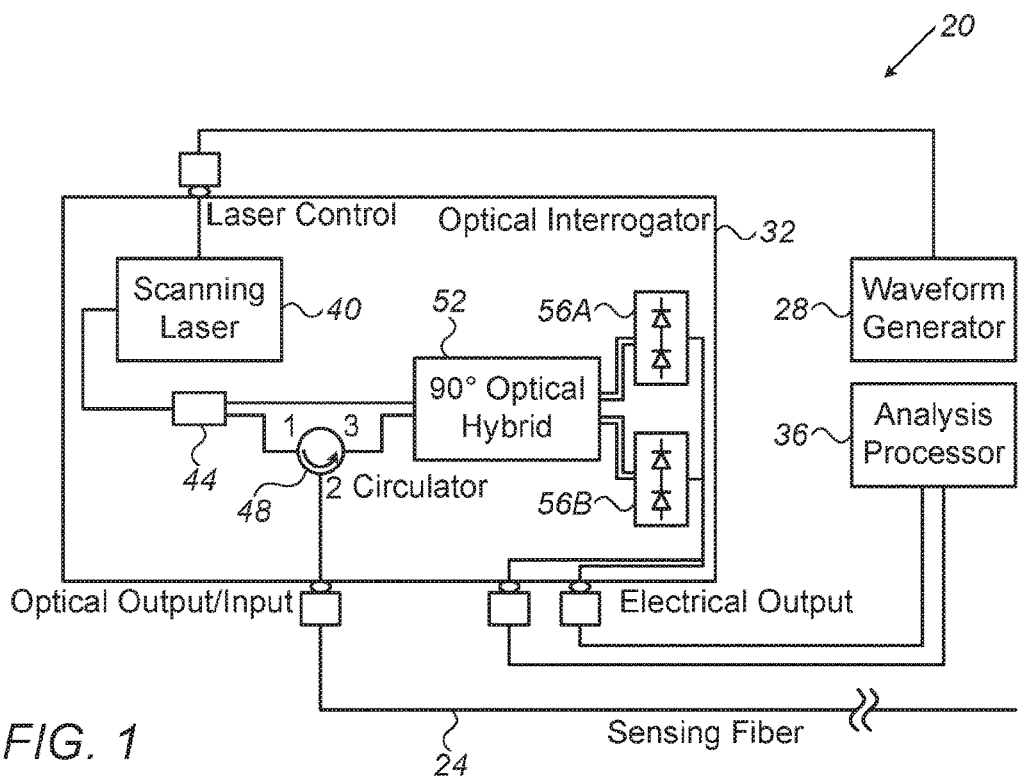
FIG. 1 is a block diagram that schematically illustrates a fiber-optic reflectometry system that uses sinusoidal frequency scanning, in accordance with an embodiment of the present invention.

Optical Frequency-Domain Reflectometry (OFDR) may be implemented by generating an optical signal whose instantaneous optical frequency varies linearly with time. In such an implementation, the optical signal is transmitted through an optical fiber, the backscattered optical signal received from the fiber is mixed with a replica of the original optical signal, and the resulting beat signal is analyzed in the frequency domain.

In the above naïve implementation, it is possible to derive spatial information from the beat signal with relatively simple frequency-domain analysis, because of the linear dependence of the instantaneous optical frequency of the optical signal on time. In practice, however, it is highly challenging to generate, with a sufficiently high repetition rate, an optical signal whose instantaneous frequency varies linearly with time.

When using external modulation, for example, the specification of the external Radio Frequency (RF) generator is extremely difficult to meet. Direct modulation of the laser is no less challenging, because lasers tend to distort the linear modulation. The implementation challenges are particularly severe in dynamic sensing applications, in which the optical signal is required to scan over a large bandwidth with fast scan repetition rate.

Embodiments of the present invention that are described herein provide improved methods and systems for fiber-optic reflectometry. The methods and systems described herein use a non-linearly-scanning optical interrogation signal, i.e., an optical interrogation signal whose instantaneous optical frequency is a non-linear function of time. The resulting beat signal is analyzed using a novel signal processing technique that compensates for the effects of the non-linear scanning. The embodiments described below refer mainly to sinusoidally-scanning optical interrogation signals, by way of example. The disclosed techniques, however, are in no way limited to sinusoidal scanning and may be implemented using various other types of non-linearly scanning optical interrogation signals.

In some embodiments of the present invention, an OFDR system comprises an optical source, a beat detection module and a processor. The optical source is configured to generate a sinusoidally-scanning optical interrogation signal having an instantaneous optical frequency that is a sinusoidal function of time. The beat detection module is configured to transmit this optical interrogation signal into an optical fiber, to receive the resulting optical backscattering signal from the optical fiber, and to mix the optical backscattering signal with a reference replica of the optical interrogation signal, so as to produce a beat signal.

The processor is configured to analyze the beat signal so as to sense one or more events affecting the optical fiber. The analysis is based on a predefined function, stored in the processor, which is indicative of the expected phase of the beat signal resulting from the sinusoidally-scanning optical interrogation signal as a function of position z along the optical fiber and time t. The predefined function typically depends on the bandwidth and modulating frequency of the sinusoidally-scanning optical interrogation signal, and on the group velocity of light in the fiber.

In an embodiment, the predefined function gives the complex conjugate of the exponential phase factor of the beat signal, which is expected to result from the sinusoidally-scanning optical interrogation signal. Other suitable predefined functions can also be used. Typically, the processor holds a matrix $\overline{R}$ of discrete values of the predefined function, over discrete ranges of z and t.

The processor calculates an estimate of the backscattering profile of the optical fiber, i.e., the complex-valued backscattering coefficient of the fiber as a function of position z, by applying the predefined function to the beat signal. In a typical implementation, the processor multiplies matrix $\overline{R}$ by a vector of discrete-time samples of the beat signal. The processor then analyzes the backscattering profile so as to sense events of interest.

In some embodiments, the above process is repeated continually in multiple scanning periods of the optical interrogation signal. In each period, the processor applies the predefined function to a respective time interval of the beat signal. The processor analyzes the resulting sequence of backscattering profiles, so as to detect dynamic changes in the fiber.

The methods and systems described herein exploit the implementation benefits of using a sinusoidally-scanning or other non-linearly scanning optical interrogation signal, without compromising performance measures such as resolution and update rate. Example experimental results are provided further below. Additional experimental results and performance data of such a system can be found in U.S. Provisional Patent Application 62/133,392, cited above, and in an article by Leviatan and Eyal, entitled "High resolution DAS via sinusoidal frequency scan OFDR (SFS-OFDR)," Optics Express, volume 23, issue 26, December, 2015, pages 33318-33334, which is incorporated herein by reference.

The disclosed techniques can be used for implementing various types of sensors for use in a wide variety of Dynamic Acoustic Sensing (DAS) applications. Example applications include optical network monitoring, perimeter security, as well as monitoring of infrastructure such as pipelines, railways and roads, to name just a few.

System Description

FIG. 1 is a block diagram that schematically illustrates a fiber-optic reflectometry system 20 that uses sinusoidal frequency scanning, in accordance with an embodiment of the present invention. System 20 transmits an optical signal through an optical fiber 24, referred to as a sensing fiber, and analyzes the optical signal reflected from the fiber. In particular, system 20 detects backscattering from various reflectors at various points along fiber 24, and estimates the locations along the fiber at which such backscattering occur.

Backscattering may be caused by distributed elastic scattering in the fiber (Rayleigh scattering), by permanent or transient mechanical faults or deformations in the fiber, or by any other suitable phenomenon or event that affects the fiber's optical properties at certain points. Detection and analysis of backscattering may serve as a basis for a wide variety of sensing applications, as will be elaborated below.

In the present example, system 20 comprises a waveform generator 28, an optical interrogation unit 32, and an analysis processor 36. Optical interrogation unit comprises a scanning laser 40, an optical splitter 44, a circulator 48, a 90° optical hybrid 52, and a pair of balanced optical detectors 56A and 56B (also referred to as optical receivers). Hybrid 52 may also be referred to as an I/Q or quadrature hybrid, mixer, demodulator or downconverter.

Waveform generator 28 generates an electrical signal having a time-varying waveform that modulates the optical frequency (the wavelength) of laser 40. As a result, laser 40 generates an optical signal whose instantaneous optical frequency varies as a function of time. In the present example waveform generator 28 generates an electrical signal having a sinusoidal waveform, which cause laser 40 to produce an optical signal whose instantaneous optical frequency is a sinusoidal function of time.

The optical signal produced by laser 40 is split using splitter 44 into an interrogation signal and a reference signal. The interrogation signal is launched into sensing fiber 24, and a backscattering signal is received from the fiber in response. The received backscattering signal is mixed with the reference signal to produce a beat signal that is in turn analyzed.

In the example of FIG. 1, the interrogation signal is transmitted via circulator 48 (via ports 1⇒2 of the circulator) into fiber 24. The reference signal (a reference replica of the interrogation signal) is applied to the Local Oscillator (LO) port of hybrid 52. The interrogation signal is reflected (e.g., backscattered) from various points along fiber 24. The superposition of these reflections, which returns from fiber 24 to interrogation unit 32, is an optical signal referred to herein as the backscattered signal. The backscattered signal passes through circulator 48 (via ports 2⇒3 of the circulator) and is applied to the signal port of hybrid 52.

Hybrid 52 has two pairs of output fibers that are connected respectively to balanced optical detectors 56A and 56B. Detectors 56A and 56B produce respective electrical signals that represent the In-phase (I) and Quadrature (Q) components of the beat signal (the backscattered signal after it has been down-converted by mixing with the reference signal). In other words, detectors 56A and 56B produce a complex-valued signal representation of the light backscattered in fiber 24.

The pair of electrical signals (i.e., the complex-valued beat signal) produced by detectors 56A and 56B is provided to analysis processor 36. Processor 36 digitizes the complex-valued beat signal and analyzes it in the frequency domain, so as to detect and localize the points along fiber 24 at which backscattering occurs. Typically, processor 36 transforms the beat signal into the frequency domain, e.g., by applying a Fourier transform, so as to produce a frequency-domain backscattering profile of the fiber. Generally speaking, each beat frequency (and thus each frequency bin of the Fourier transform) is mapped to a respective location along the fiber. The functions of processor 36 are addressed in greater detail further below.

The configuration of system 20 shown in FIG. 1 is an example configuration, which is chosen purely for the sake of conceptual clarity. In alternative embodiments, any other suitable system configuration can be used. For example, the configuration of FIG. 1 uses direct modulation of laser 40. Alternatively, the disclosed techniques can be used in systems that externally modulate the wavelength of the optical signal produced by the laser, or in systems that generate a scanning optical signal in any other suitable manner.

In the present context, waveform generator 28 and laser 40 are referred to jointly as an optical source. Splitter 44, circulator 48, hybrid 52 and detectors 56A and 56B are referred to jointly as a beat detection module. In alternative embodiments, system 20 may be implemented using any other suitable configuration of the optical source and/or beat detection module.

The different elements of system 20 may be implemented using various suitable optical and/or electronic hardware components, integrated or discrete. System elements that are not mandatory for understanding of the disclosed techniques have been omitted from the figure for the sake of clarity. Further aspects of this system configuration are also described in PCT Application PCT/IB2015/058819, entitled "Spectrally Efficient Optical Frequency-Domain Reflectometry using I/Q Detection," which is assigned to the assignee of the present patent application and whose disclosure is incorporated herein by reference.

In one example embodiment, fiber 24 comprises a Corning SMF-28 fiber, laser 40 comprises a tunable laser by Koheras Adjustik of NKT Photonics having a central wavelength of 1550 nm. Waveform generator 28 modulates the instantaneous optical frequency of laser 40 by applying the sinusoidal electrical signal to an internal piezo-electric actuator (PZT) in the laser. Splitter 44 comprises a TW1550R5A2 device provided by Thorlabs, circulator 48 comprises a 6015-3-APC device provided by Thorlabs, hybrid 52 comprises a COH24-X device provided by Kylia, detectors 56A and 56B comprise PDB470C-AC devices provided by Thorlabs. In alternative embodiments, however, any other suitable components can be used.

Some system elements, e.g., waveform generator 28, may be implemented using off-the-shelf or modified test equipment. Some system elements, e.g., analysis processor 36, may be implemented using hardware, e.g., using one or more Application-Specific Integrated Circuits (ASICs) or Field-Programmable Gate Arrays (FPGAs), using software, or using a combination of hardware and software elements.

In some embodiments, processor 36 may be implemented using one or more general-purpose processors, which are programmed in software to carry out the functions described herein. The software may be downloaded to the processors in electronic form, over a network, for example, or it may, alternatively or additionally, be provided and/or stored on non-transitory tangible media, such as magnetic, optical, or electronic memory.

OFDR Analysis Based on Sinusoidal Frequency Scanning Interrogation Signal

As noted above, in some embodiments the instantaneous optical frequency of laser 40 is a sinusoidal function of time. The instantaneous optical frequency of the laser in these embodiments can be written as $$f_{inst} = f_0 + \frac{\Delta F}{2} \sin(\omega_r t) \quad [1]$$

wherein $f_0$ denotes the nominal center frequency of the laser at t=0, $\Delta F$ denotes the bandwidth scanned by the optical interrogation signal, and $\omega_r = 2\pi f_r$ denotes the angular frequency with which the laser is modulated. In other words, $f_r$ denotes the frequency of the sinusoidal modulating signal generated by waveform generator 28.

The electrical field of the optical interrogation signal is thus given by $$E_{in}(t) = E_0 \exp\left\{i 2\pi \left[f_0 t - \frac{\Delta F}{2\omega_r} \cos(\omega_r t)\right]\right\} \quad [2]$$

Sensing fiber 24 can be modeled as a distributed reflector along the z-dimension, having a complex-valued z-dependent backscatter coefficient denoted $\rho(z)$. The backscattered field is given by $$E_B(t) = \int_0^L \rho(z') E_{in}\left(t - \frac{2z'}{v_g}\right) \exp[i\Phi(z')] dz' \quad [3]$$

wherein L denotes the length of fiber 24, $v_g$ denotes the group velocity of light in fiber 24, and $\Phi(z)$ denotes the accumulated round-trip phase of the field that was backscattered from position z along fiber 24.

When using the sinusoidally-scanning interrogation signal defined above, the complex-valued beat signal V(t)=I(t)+iQ(t) at the output of detectors 56A and 56B can be written as $$V(t) = A \int_0^L \tilde{\rho}(z') \exp\left\{i \frac{\pi \Delta F}{\omega_r} \left[\cos\left(\omega_r\left(t - \frac{2z'}{v_g}\right)\right) - \cos(\omega_r t)\right]\right\} dz' \quad [4]$$

wherein A is a constant describing the responsivity and gain of the I/Q demodulator and detectors, and $\tilde{\rho}(z)$ denotes the complex-valued backscatter coefficient at position z. The backscatter coefficient $\tilde{\rho}(z)$ is defined as $$\tilde{\rho}(z) \equiv \rho(z) \exp\left\{i\left[\omega_0 \frac{2z}{v_g} - \Phi(z)\right]\right\} \quad [5]$$

(As can be seen in Equation [4], the instantaneous optical frequency can have both positive and negative values. Therefore, to fully exploit the information conveyed in the beat signal V(t), Quadrature (I/Q) detection is used. In alternative embodiments, however, system 20 may nevertheless be implemented using real-valued detection, with somewhat reduced performance.)

An estimate of the complex-valued backscatter coefficient can be written as $$\hat{\tilde{\rho}}(z) = \int_{-T/2}^{T/2} V(t) \exp\left\{-i \frac{\pi \Delta F}{\omega_r} \left[\cos\left(\omega_r\left(t - \frac{2z}{v_g}\right)\right) - \cos(\omega_r t)\right]\right\} dz \quad [6]$$

wherein T is the interrogation time interval over which the beat signal V(t) is sampled.

Equation [6] can be viewed as a projection of the beat signal V(t) onto the function $$R(z, t) = \exp\left\{-i \frac{\pi \Delta F}{\omega_r} \left[\cos\left(\omega_r\left(t - \frac{2z}{v_g}\right)\right) - \cos(\omega_r t)\right]\right\} \quad [7]$$

The function R(z,t) in [7] is indicative of the expected backscattering profile of fiber 24, when interrogated by a sinusoidal interrogation signal having an angular frequency $\omega_r$ and bandwidth $\Delta F$.

For given values of z, t, R(z,t) gives the complex conjugate of the exponential phase factor of the beat signal, which is expected to result from backscattering of the sinusoidally-scanning optical interrogation signal from position z, after t seconds from the beginning of the current scanning period.

In other words, for a given z, R(z,t) is indicative of the expected phase of the signal that is backscattered from position z, as a function of time. Note that R(z,t) depends only on the scan parameters ($\omega_r$ and $\Delta F$), and on the light velocity in the fiber ($v_g$). Function R(z,t) is predefined in the sense that it does not depend on the actual real-time values of the interrogation or backscattering signals. As such, function R(z,t) can therefore be computed and stored in advance, before actual interrogation of the fiber is initiated.

In some embodiments, analysis processor 36 estimates the complex-valued backscatter coefficient $\hat{\tilde{\rho}}(z)$ by calculating the integral in Equation [6], using the actual received beat signal V(t) and the known function R(z,t).

Typically, however, processor 36 evaluates a discrete-time version of Equation [6]. In these embodiments, processor 36 pre-computes a matrix $\overline{R}$, whose vertical dimension corresponds to position z along the fiber, and whose horizontal dimension corresponds to time.

Figure 2:
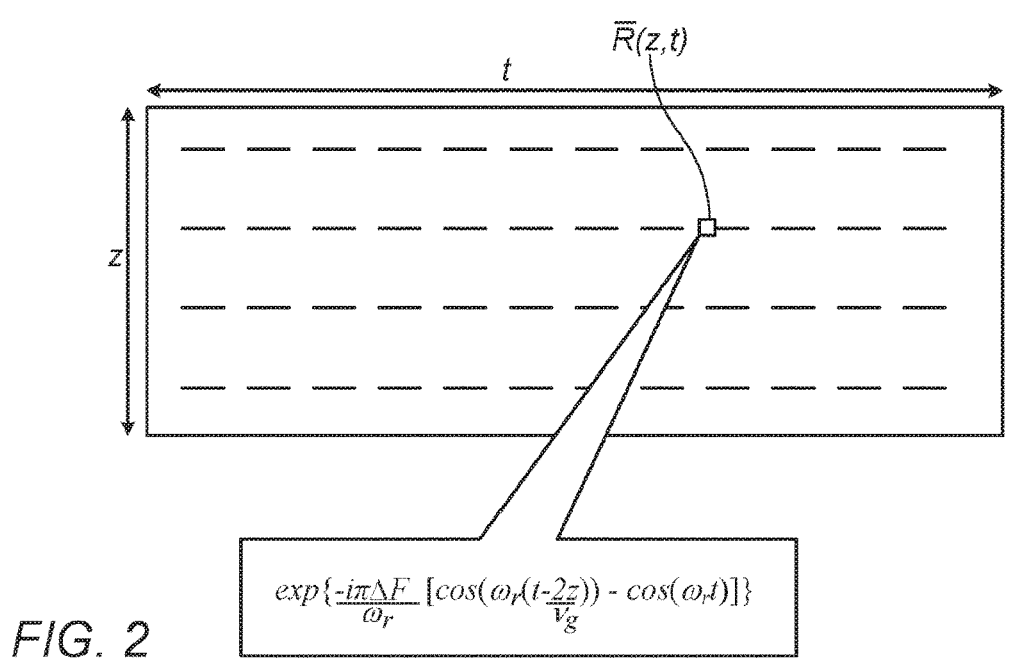
FIG. 2 is a diagram that schematically illustrates a pre-computed matrix of expected fiber profiles under sinusoidal frequency scanning, in accordance with an embodiment of the present invention.

FIG. 2 is a diagram that schematically illustrates the pre-computed matrix $\overline{R}$, in accordance with an embodiment of the present invention. The matrix element on the $z^{th}$ row and $i^{th}$ column of matrix $\overline{R}$ (with z and t being discrete values) gives the complex conjugate of the exponential phase factor of the beat signal, which is expected to result from backscattering of the sinusoidally-scanning optical interrogation signal from position z, after t seconds from the beginning of the current scanning period. In other words, the $z^{th}$ row of matrix $\overline{R}$ gives the expected conjugate phase factor of the signal that is backscattered from position z, as a function of time.

In these embodiments, processor 36 digitizes the complex-valued beat signal V(t), e.g., using a pair of Analog to Digital Converters (ADCs), over the interrogation time interval. Processor 36 then multiplies matrix $\overline{R}$ by the vector of the sampled beat signal. The resulting vector gives the backscattering profile of fiber 24—The estimated complex-valued backscattering coefficient $\hat{\rho}(z)$ as a function of z.

The row size (the number of columns) of matrix $\overline{R}$ is the number of samples in the interrogation time interval. For a sampling frequency of 1 G samples per second and a time interval of 10 μS, the number of samples is 10,000. The column size (the number of rows) of matrix $\overline{R}$ depends on the length of fiber 24 and on the spatial resolution used. For a 10 km fiber and a spatial resolution of 1 meter, the column size is 10,000. Alternatively, any other suitable row and column sizes can be used.

The embodiments described herein refer to a sinusoidally-scanning optical interrogation signal, whose instantaneous frequency as a function of time is a sinusoid. The disclosed techniques, however, are in no way limited to sinusoidally-scanning optical interrogation signals, or to the specific predefined function of Equation [7]. In alternative embodiments, the optical source (generator 28 and laser 40) may generate any other suitable type of periodic optical interrogation signal whose instantaneous frequency, within each scanning period, is a non-linear function of time. Processor 36 may use any suitable predefined function that is indicative of the expected phase of the beat signal resulting from such a periodic, non-linearly-scanning optical interrogation signal as a function of z and t.

For example, the instantaneous frequency of the optical interrogation signal may be a sum of two or more sinusoidal harmonics or any other periodic function of time. In this case the expected phase of the beat signal will be pre-computed accordingly. Note that the predefined function does not account for the (slowly-varying frequency-independent) phase that the optical signal acquires in its round-trip along the fiber.

Figure 3:
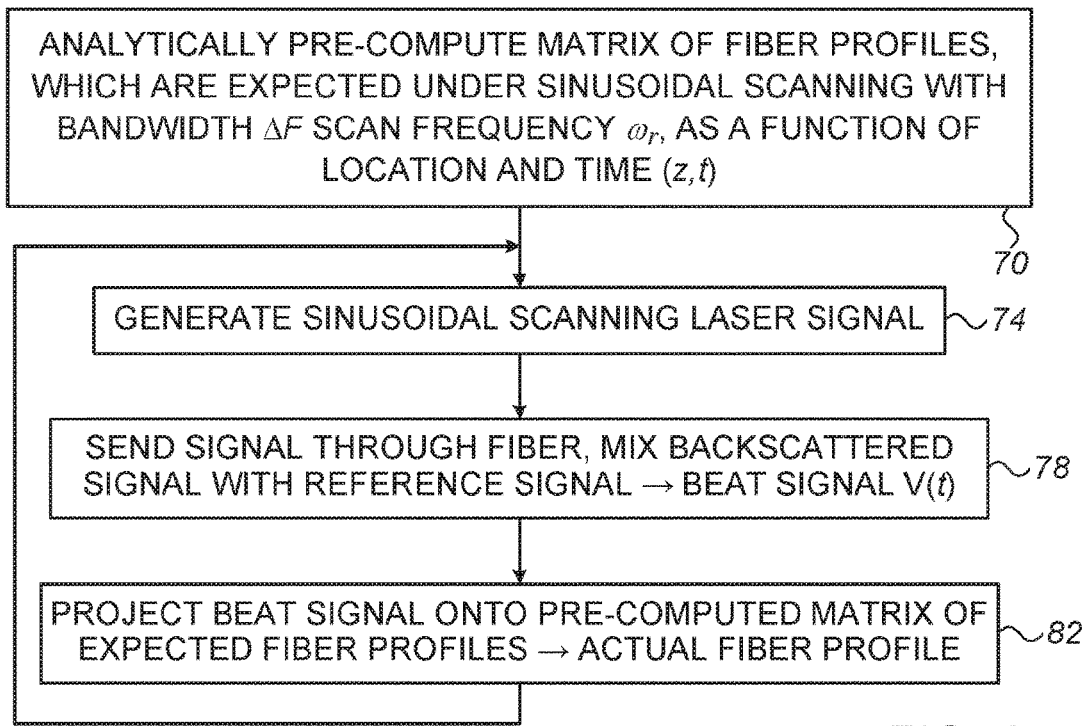
FIG. 3 is a flow chart that schematically illustrates a method for fiber-optic reflectometry using sinusoidal frequency scanning, in accordance with an embodiment of the present invention.

FIG. 3 is a flow chart that schematically illustrates a method for fiber-optic reflectometry using sinusoidal frequency scanning, in accordance with an embodiment of the present invention. The method begins with processor 36 of system 20 pre-computing and storing the predefined matrix $\overline{R}$ shown in FIG. 2, at a pre-computation step 70. Alternatively, matrix $\overline{R}$ may be computed by some other processor and provided to processor 20 in advance.

At a signal generation step 74, the optical source of system 20 generates a sinusoidally-scanning interrogation signal. The parameters of the interrogation signal ($\omega_r$ and $\Delta F$) should match the parameters for which matrix $\overline{R}$ was pre-computed.

At a beat-signal generation step 78, the beat detection module of system 20 sends the interrogation signal through fiber 24, and mixes the resulting backscattered signal with a reference replica of the interrogation signal, so as to produce the complex-valued beat signal V(t).

At a projection step 82, processor 36 of system 20 multiplies matrix $\overline{R}$ by a vector of samples of the beat signal V(t). The vector of samples is typically acquired over a single scan period of the interrogation signal, or over a portion of such a period. This multiplication essentially performs a discrete version of Equation [6], which produces an estimate of the complex-valued backscatter coefficient $\hat{\rho}(z)$ as a function of z. The method then loops back to step 74 above, for processing another scan period.

Processor 36 thus obtains a sequence of estimates $\hat{\rho}(z)$ of the fiber backscattering profile, corresponding to a respective sequence of time intervals. Processor 36 typically generates a two dimensional matrix of the acquired profiles as a function of time.

By analyzing the time dependent fiber profile, processor 36 is able to identify temporal variations in the backscattering profile, which are indicative of transient events that affect the backscattering coefficient of the fiber. The actual events being detected depend on the application of system 20. Several example applications are described further below.

Example Experimental Results

In an example experimental setup of system 20, the length of sensing fiber 24 was ~780 m. Laser 40 was modulated with an electrical signal having a frequency of 21 KHz and an amplitude of 10V. This electrical signal was applied to the internal piezo-electric actuator (PZT) of laser 40 with a conversion efficiency of K(21 KHz)=18.7 MHz/V. The peak-to-peak scan bandwidth (Δf) of the resulting interrogation signal was ~373.5 MHz. The beat signal V(t) was sampled over 12 μS intervals (25% of the modulation period), and a total of 5000 such intervals were acquired, spanning a total time of ~238 mS.

Various tests were conducted using this setup. Comprehensive test results are given in U.S. Provisional Patent Application 62/133,392, and in the article "High resolution DAS via sinusoidal frequency scan OFDR (SFS-OFDR)," cited above.

Figure 4A:
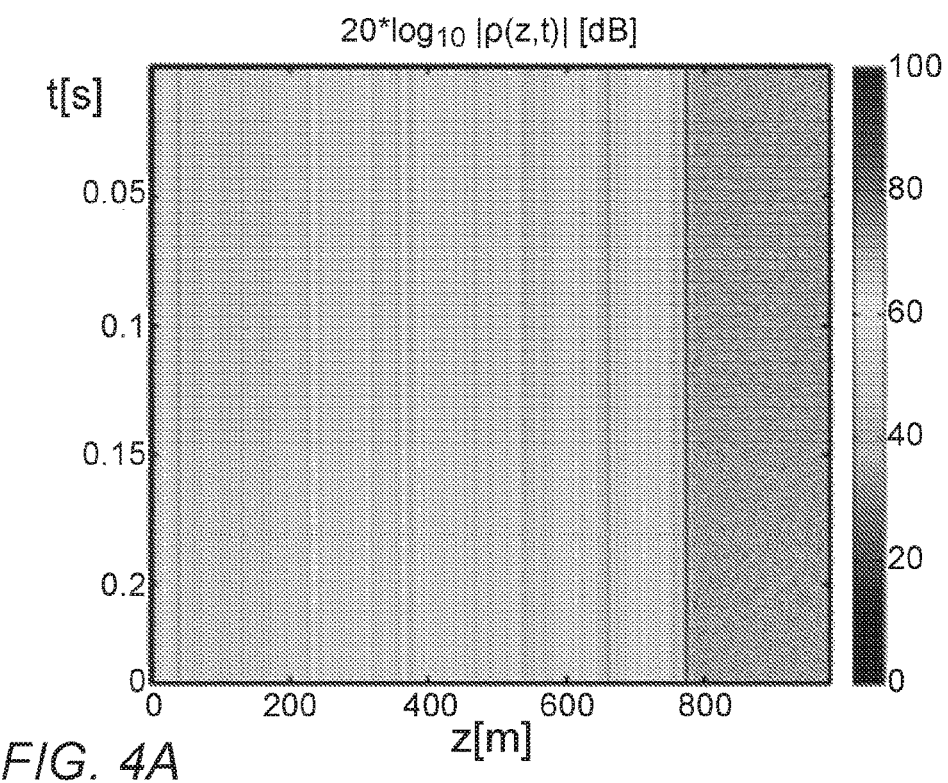
FIGS. 4A-4C are graphs showing example experimental results of a fiber-optic reflectometry system that uses sinusoidal frequency scanning, in accordance with an embodiment of the present invention.
Figure 4B:
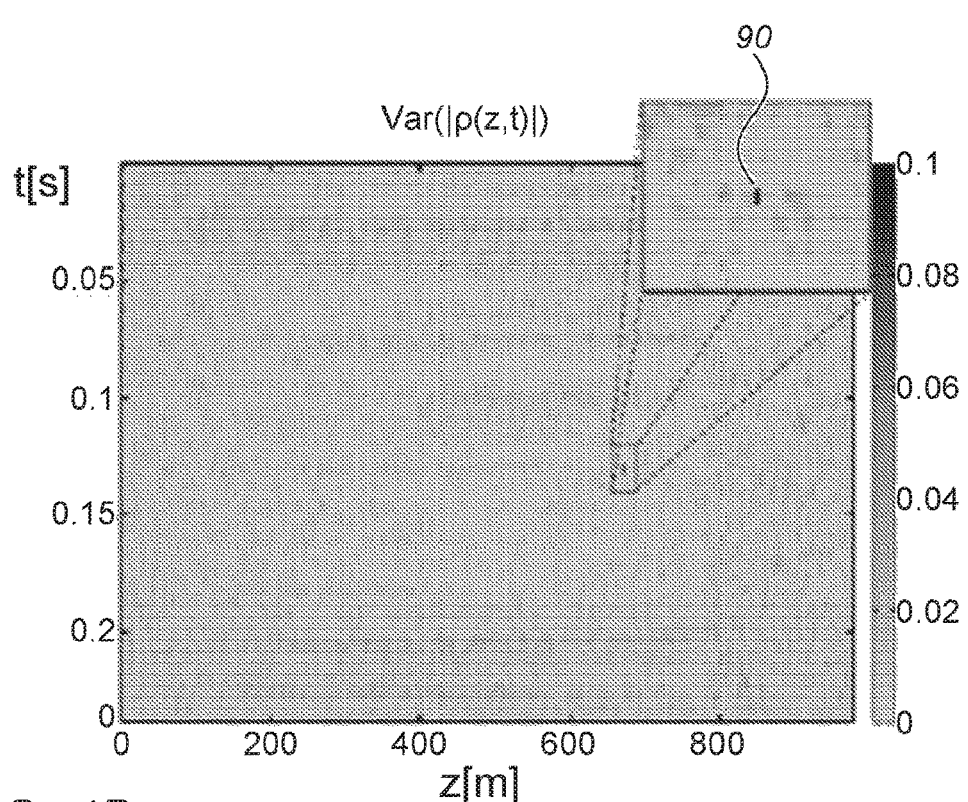
Figure 4C:
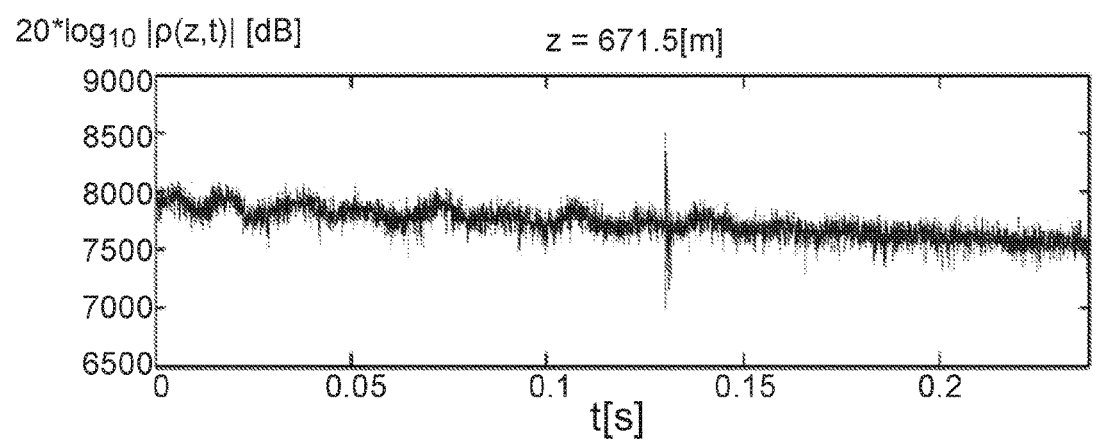

FIGS. 4A-4C are graphs showing example experimental results of system 20, in accordance with an embodiment of the present invention. In this particular experiment, a section of fiber 24 was buried under ~1 cm of sand, and a paperclip was dropped on the sand from a height of ~5 cm.

FIG. 4A shows the measured time-dependent backscattering profile of the fiber.

FIG. 4B shows the variance of the backscattering profile as a function of time and position. The variance was calculated for each position along the fiber using a sliding window of 100 modulation periods (a total time of ~4.76 mS). A burst 90 of high variance can be seen clearly in the top-right inset in the figure. Burst 90 indicates the time and position at which the paperclip was dropped. The width of burst 90 indicates a dynamic spatial resolution of ~0.6 m.

FIG. 4C shows the time dependence of the backscattering profile of the fiber at the position of burst 90 (z≈671.5 m). The paperclip drop event can be seen very clearly in the figure.

Example Applications

In various embodiments, systems such as system 20 of FIG. 1 can be used in a wide variety of applications that involve detecting various kinds of events that affect an optical-fiber. Typically, although not necessarily, system 20 is used in dynamic sensing applications that benefit from fast update rate.

In some embodiments, system 20 is used for monitoring optical fibers in an optical communication network, for example in order to detect and locate faults in the fibers. In this application, the sensed events are typically faults in the optical fiber that impact the communication performance of the network.

In other embodiments, sensing fiber 24 is installed as part of a perimeter security system for protecting a certain area or structure. In such applications, the sensed events typically relate to illegitimate entry, i.e., illegitimate breach of the perimeter security system.

In other embodiments, sensing fiber 24 is installed in some utility infrastructure element, in order to detect fatigue-related faults or other faults in the infrastructure. The fiber may be installed, for example, in an oil or water pipeline, in a railway line or in a road or bridge. In this sort of application, the sensed events are typically related to faults in the infrastructure element.

The applications listed above are depicted purely by way of example. In alternative embodiments, the disclosed techniques can be used as part of any other suitable system and for any other suitable application.

Although the embodiments described herein mainly address sensing of direct static or dynamic mechanical perturbations to the sensing fiber, the methods and systems described herein can also be used in other applications where other measurands, such as temperature, current, magnetic field, electric field or pressure, are transformed by suitable transduction mechanism to mechanical perturbations in the sensing fiber.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for fiber-optic reflectometry, the system comprising:
   an optical source, which is configured to generate a non-linearly-scanning optical interrogation signal having an instantaneous optical frequency that is a non-linear function of time;
   a beat detection module, which is configured to transmit the optical interrogation signal into an optical fiber, to receive from the optical fiber an optical backscattering signal in response to the optical interrogation signal, and to mix the optical backscattering signal with a reference replica of the optical interrogation signal, so as to produce a beat signal; and
   a processor, which is configured (i) to hold a predefined function that is indicative of an expected phase of the beat signal resulting from the non-linearly-scanning optical interrogation signal as a function of position along the optical fiber and time, (ii) to estimate a backscattering profile of the optical fiber by applying the predefined function to the beat signal, and (iii) to sense one or more events affecting the optical fiber by analyzing the backscattering profile.

2. The system according to claim 1, wherein the instantaneous optical frequency of the optical interrogation signal is a sinusoidal function of time.

3. The system according to claim 1, wherein the predefined function specifies a complex conjugate of an exponential phase factor of the beat signal, which is expected to result from the non-linearly-scanning optical interrogation signal, as a function of the position and the time.

4. The system according to claim 1, wherein the processor is configured to hold a matrix of discrete values of the predefined function, and to apply the predefined function to the beat signal by multiplying the matrix by a vector of samples of the beat signal.

5. The system according to claim 1, wherein the processor is configured to calculate multiple successive estimates of the backscattering profile, by applying the predefined function to multiple respective time periods of the beat signal, and to sense the events by analyzing the multiple successive estimates of the backscattering profile.

6. The system according to claim 1, wherein the optical source is configured to generate the non-linearly-scanning optical interrogation signal with a given bandwidth and a given modulation frequency, and wherein the predefined function depends on the given bandwidth and the given modulation frequency.

7. The system according to claim 1, wherein the beat detection module is configured to mix the optical backscattering signal with the reference replica of the optical interrogation signal using In-phase/Quadrature (I/Q) mixing, such that the beat signal is complex-valued.

8. The system according to claim 1, wherein the optical fiber is part of an optical communication system, and wherein the one or more events comprise a fault in the optical fiber.

9. The system according to claim 1, wherein the optical fiber is part of a perimeter security system, and wherein the one or more events comprise a breach of the perimeter security system.

10. The system according to claim 1, wherein the optical fiber is installed in a utility infrastructure, and wherein the one or more events comprise a fault in the utility infrastructure.

11. A method for fiber-optic reflectometry, the method comprising:
   generating a non-linearly-scanning optical interrogation signal having an instantaneous optical frequency that is a non-linear function of time;
   transmitting the optical interrogation signal into an optical fiber, receiving from the optical fiber an optical backscattering signal in response to the optical interrogation signal, and mixing the optical backscattering signal with a reference replica of the optical interrogation signal, so as to produce a beat signal;
   estimating a backscattering profile of the optical fiber, by applying to the beat signal a predefined function that is indicative of an expected phase of the beat signal resulting from the non-linearly-scanning optical interrogation signal as a function of position along the optical fiber and time; and
   sensing one or more events affecting the optical fiber by analyzing the backscattering profile.

12. The method according to claim 11, wherein the instantaneous optical frequency of the optical interrogation signal is a sinusoidal function of time.

13. The method according to claim 11, wherein the predefined function specifies a complex conjugate of an exponential phase factor of the beat signal, which is expected to result from the non-linearly-scanning optical interrogation signal, as a function of the position and the time.

14. The method according to claim 11, and comprising holding a matrix of discrete values of the predefined function, wherein applying the predefined function to the beat signal comprises multiplying the matrix by a vector of samples of the beat signal.

15. The method according to claim 11, wherein estimating the backscattering profile comprises calculating multiple successive estimates of the backscattering profile by applying the predefined function to multiple respective time periods of the beat signal, and wherein sensing the events comprises analyzing the multiple successive estimates of the backscattering profile.

16. The method according to claim 11, wherein generating the non-linearly-scanning optical interrogation signal comprises producing the non-linearly-scanning optical interrogation signal with a given bandwidth and a given modulation frequency, and wherein the predefined function depends on the given bandwidth and the given modulation frequency.

17. The method according to claim 11, wherein mixing the optical backscattering signal with the reference replica of the optical interrogation signal comprises applying In-phase/Quadrature (I/Q) mixing, such that the beat signal is complex-valued.

18. The method according to claim 11, wherein the optical fiber is part of an optical communication system, and wherein sensing the events comprises sensing a fault in the optical fiber.

19. The method according to claim 11, wherein the optical fiber is part of a perimeter security system, and wherein sensing the events comprises sensing a breach of the perimeter security system.

20. The method according to claim 11, wherein the optical fiber is installed in a utility infrastructure, and wherein sensing the events comprises sensing a fault in the utility infrastructure.

* * * * *